United States Patent
Pongpeerapat et al.

(10) Patent No.: US 10,022,340 B2
(45) Date of Patent: Jul. 17, 2018

(54) TOPICAL SPHINGOSINE-1-PHOSPHATE RECEPTOR AGONIST FORMULATIONS AND METHODS OF USING THE SAME

(71) Applicant: Teikoku Pharma USA, Inc., San Jose, CA (US)

(72) Inventors: Adchara Pongpeerapat, San Jose, CA (US); Bret Berner, Half Moon Bay, CA (US); Kensuke Murata, Santa Clara, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 334 days.

(21) Appl. No.: 14/473,462

(22) Filed: Aug. 29, 2014

(65) Prior Publication Data

US 2015/0104497 A1    Apr. 16, 2015

Related U.S. Application Data

(60) Provisional application No. 61/890,066, filed on Oct. 11, 2013.

(51) Int. Cl.
| | |
|---|---|
| A61K 9/70 | (2006.01) |
| A61K 31/137 | (2006.01) |
| A61K 9/00 | (2006.01) |
| A61K 9/06 | (2006.01) |
| A61K 47/38 | (2006.01) |
| A61K 47/14 | (2017.01) |
| A61K 47/20 | (2006.01) |
| A61K 47/32 | (2006.01) |

(52) U.S. Cl.
CPC .......... *A61K 31/137* (2013.01); *A61K 9/0014* (2013.01); *A61K 9/06* (2013.01); *A61K 9/7061* (2013.01); *A61K 47/38* (2013.01); *A61K 47/14* (2013.01); *A61K 47/20* (2013.01); *A61K 47/32* (2013.01)

(58) Field of Classification Search
CPC ...... A61K 47/12; A61K 47/38; A61K 31/185; A61K 31/194; A61K 31/197; A61K 31/20; A61K 31/216; A61K 31/22; A61K 31/26
See application file for complete search history.

(56) References Cited

U.S. PATENT DOCUMENTS

| | | |
|---|---|---|
| 5,505,715 A | 4/1996 | Shah et al. |
| 5,604,229 A | 2/1997 | Fujita et al. |
| 6,004,565 A | 12/1999 | Chiba et al. |
| 6,121,329 A | 9/2000 | Fujii et al. |
| 7,151,093 B2 | 12/2006 | Kishikawa et al. |
| 2005/0090520 A1 | 4/2005 | Lindquist |
| 2005/0232983 A1* | 10/2005 | Sandage, Jr. ...... A61K 31/4745 424/449 |
| 2009/0176744 A1 | 7/2009 | Liu et al. |
| 2009/0275553 A1 | 11/2009 | Kovarik et al. |
| 2010/0112037 A1* | 5/2010 | Bachrach ............. A61K 9/0014 424/449 |
| 2010/0160259 A1 | 6/2010 | Schmouder et al. |
| 2010/0168078 A1 | 7/2010 | Hiestand et al. |
| 2012/0285618 A1 | 11/2012 | Bharti et al. |
| 2013/0090588 A1 | 4/2013 | Buus et al. |
| 2017/0333410 A1* | 11/2017 | Babul .................. A61K 31/445 |

FOREIGN PATENT DOCUMENTS

| | | |
|---|---|---|
| EP | 2255798 A2 | 12/2010 |
| JP | 2012-507546 A | 3/2012 |
| WO | WO2010051349 A1 | 5/2010 |
| WO | WO20100055027 A3 | 5/2010 |

OTHER PUBLICATIONS

Kappos et al., A Placebo-Controlled Trial of Oral Fingolimod in Relapsing Multiple Sclerosis, the New England Journal of Medicine (2010), 362(5):387-401.
Cohen et al., Oral Fingolimod or Intramuscular Interferon for Relapsing Multiple Sclerosis, the New England Journal of Medicine (2010), 362(5):402-415.
Mitsubishi UFJ Securities, Unment medical needs key, Japan Equity Research, Industry Update, Oct. 9, 2009, 19 pages.
Duro-Tak and Gelva Transdermal Pressure Sensitive Adhesives, Product Selection Guide, Sep. 2013, 2 pages.
Yamauchi et al., Development and Application of Next-Generation Transdermal Absorption Formulations, Jul. 29, 2011, CMC Books, 1st printing, p. 224-229, Abstract Only.

\* cited by examiner

*Primary Examiner* — Nannette Holloman
(74) *Attorney, Agent, or Firm* — Khin K. Chin; Bret E. Field; Bozicevic, Field & Francis LLP

(57) ABSTRACT

Topical sphingosine-1-phosphate receptor agonist active agent formulations are provided. Aspects of the transdermal formulations include an amount of a sphingosine-1-phosphate receptor agonist active agent in combination with a topical delivery vehicle, e.g., a topical patch that includes an adhesive layer and a backing layer. Also provided are methods of topically delivering a therapeutically effective amount of a sphingosine-1-phosphate receptor agonist active agent to a subject, e.g., to treat a subject for a disease condition, such as an immune system disorder like multiple sclerosis, a hyperproliferative dermatological disorder, e.g., psoriasis, acne, etc. Packaged topical formulations, kits including such formulations, and methods of making such formulations are also provided.

21 Claims, 7 Drawing Sheets

TOPICAL SPHINGOSINE-1-PHOSPHATE RECEPTOR AGONIST FORMULATIONS AND METHODS OF USING THE SAME

CROSS-REFERENCE TO RELATED APPLICATIONS

Pursuant to 35 U.S.C. § 119(e), this application claims priority to the filing date of U.S. Provisional Application Ser. No. 61/890,066 filed Oct. 11, 2013, the disclosure of which is herein incorporated by reference.

INTRODUCTION

Nerve cells communicate by sending electrical signals, or action potentials, down long fibers called axons, which are wrapped in a fatty insulating substance called myelin. Multiple sclerosis (MS) is a disease in which the fatty myelin sheaths around the nerve axons of the brain and spinal cord are damaged, leading to demyelination and scarring of the axons. MS affects the ability of nerve cells in the brain and spinal cord to communicate with each other. In MS, the body's own immune system attacks and damages the myelin. When myelin is lost, the axons can no longer effectively conduct electrical signals.

Modulators of sphingosine-1-phosphate receptors have been developed for the treatment of inflammatory disorders and autoimmune conditions. For example, a 2-amino-1,3-propanediol compound designated fingolimod (a.k.a. FTY720) is a sphingosine-1-phosphate receptor agonist that has immunosuppressive activity. Fingolimod is derived from the myriocin (a.k.a. ISP-1) metabolite of the fungus *Isaria sinclairii*. Fingolimod is a structural analogue of sphingosine and is phosphorylated by sphingosine kinases in the cell. Fingolimod acts by sequestering lymphocytes in lymph nodes, preventing the lymphocytes from moving to other regions of the body, e.g., the central nervous system where they can play a role in autoimmune responses such as those underlying multiple sclerosis. It is believed that Fingolimod is effective for the treatment of MS due to its ability to sequester myelin antigen-specific CD4 T cells and IFN-gamma type 1 helper T cells into the lymph nodes, reducing the infiltration of these T cells into the CNS where they are free to damage the myelin sheaths around the nerve axons.

SUMMARY

Topical sphingosine-1-phosphate receptor agonist active agent formulations are provided. Aspects of the transdermal formulations include an amount of a sphingosine-1-phosphate receptor agonist active agent in combination with a topical delivery vehicle, e.g., a topical patch that includes an adhesive layer and a backing layer. Also provided are methods of topically delivering a therapeutically effective amount of a sphingosine-1-phosphate receptor agonist active agent to a subject, e.g., to treat a subject for a disease condition, such as an immune system disorder like multiple sclerosis, a hyperproliferative dermatological disorder, e.g., psoriasis, acne, etc. Packaged topical formulations, kits including such formulations, and methods of making such formulations are also provided.

DETAILED DESCRIPTION

Figure 1:
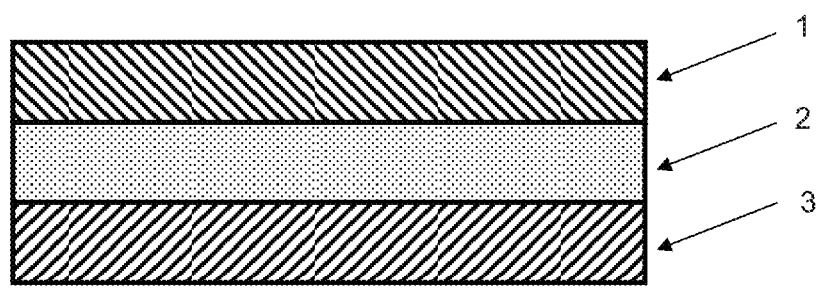
FIG. 1 provides a schematic of a topical patch formulation according to an aspect of the invention.

Topical sphingosine-1-phosphate receptor agonist active agent formulations are provided. Aspects of the transdermal formulations include an amount of a sphingosine-1-phosphate receptor agonist active agent in combination with a topical delivery vehicle, e.g., a topical patch that includes an adhesive layer and a backing layer. Also provided are methods of topically delivering a therapeutically effective amount of a sphingosine-1-phosphate receptor agonist active agent to a subject, e.g., to treat a subject for a disease condition, such as an immune system disorder like multiple sclerosis, a hyperproliferative dermatological disorder, e.g., psoriasis, acne, etc. Packaged topical formulations, kits including such formulations, and methods of making such formulations are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the invention, embodiments of the topical formulations will be described first in greater detail. Thereafter, aspects of embodiments of the methods are described in greater detail. Next, aspects of embodiments of the packaged formulations, kits, and methods of making the transdermal formulations are described in greater detail.

Topical Formulations

As summarized above, topical formulations of a sphingosine-1-phosphate receptor agonist active agent are provided. The term "topical" is used herein to refer to either or both local cutaneous and systemic therapeutic delivery of an active agent. As such, topical formulations may be formulations that provide for only local delivery of an active agent. Alternatively, topical formulations may be formulations that provide for systemic delivery of an active agent. Topical formulations may also be formulations that provide for both local and systemic delivery of an active agent.

The active agent component may include one or more sphingosine-1-phosphate receptor agonist active agents. As used herein, a "sphingosine-1-phosphate receptor agonist" active agent may be any compound or composition of matter that binds to one or more of the sphingosine-1-phosphate receptors of a cell, and optionally triggers a response by that cell. For example, the sphingosine-1-phosphate receptor agonist may be a compound or composition of matter that binds to sphingosine-1-phosphate receptor 1 (S1P1), sphingosine-1-phosphate receptor 2 (S1P2), sphingosine-1-phosphate receptor 3 (S1P3), sphingosine-1-phosphate receptor 4 (S1P4), or sphingosine-1-phosphate receptor 5 (S1P5), or any combination thereof. By "active agent" is meant a compound or composition of matter which, when administered to an organism (human or animal) induces a desired pharmacologic and/or physiologic effect. The active agents herein are local sphingosine-1-phosphate receptor agonists and pharmacologically acceptable salts, bases, esters, amides, derivatives, polymorphs or prodrugs thereof.

In certain aspects, the sphingosine-1-phosphate receptor agonist active agent is a 2-amino-1,3-propanediol compound, derivative thereof and/or salt thereof. For example, the sphingosine-1-phosphate receptor agonist active agent may be a 2-amino-2-[2-(4-octylphenyl)ethyl]propane-1,3-diol compound (or salt thereof) that binds to one or more of S1P1-S1P5. In one aspect, the sphingosine-1-phosphate receptor agonist active agent is fingolimod or a salt thereof. Fingolimod free base has the structure:

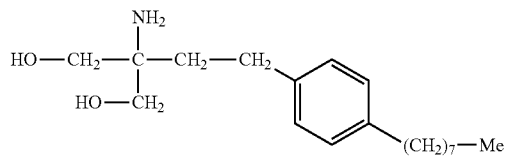

The active agent may be present in the topical formulation as a freebase or salt. Where the active agent is present as a salt, the salt may vary. In some instances, the salt is selected from chloride, bromide, maleate, fumarate, ascorbate, succinate, oxalate, phosphate, mandelate, adipate, ethanesulfonate, naphthalene-1,5-disulfonate, naphthalene-1-sulfonate, naphthalene-2-sulfonate, L-aspartate, 4-acetamidobenzoate, (+) camphorate, (+) camphor-10-sulfonate, decanoate, hexanoate, octanoate, cinnamate, dodecylsulfate, ethane-1,2-disulfonate, 2-hydroxyethanesulfonate, glutarate, DL-lactate, 1-hydroxy-2-naphthoate, laureate, salicylate, tartrate, mesylate, citrate, benzoate or mixtures thereof. Specific sphingosine-1-phosphate receptor agonist active agents of interest include, but are not limited to: fingolimod HCl, fingolimod HBr, fingolimod maleate and fingolimod fumarate. Also of interest are polymorphic forms of such agents, such as polymorphic forms of fingolimod hydrochloride. In some instances, the sphingosine-1-phosphate receptor agonist active agent is the sole or only active agent in the topical formulation.

Topical formulations are compositions that are formulated for delivery of a sphingosine-1-phosphate receptor agonist active agent to a topical location, such as a keratinized skin surface or a mucosal surface of a mammalian subject, such as a human subject. By keratinized skin surface is meant a skin location of a subject, i.e., a location of the external covering or integument of an animal body. By mucosal surface is meant a location of a subject that includes a mucosal membrane, such as the inside of the mouth, in the inside of the nose, etc. While the formulations are configured for delivery to such a location, they may provide for local and/or systemic delivery of the agent, e.g., as described above.

Because the dermal delivery formulations of the invention are formulated for delivery to topical location, they are formulated so as to be physiologically compatible with the topical location for which they are formulated. Accordingly, when contacted with the target keratinized skin surface or mucosal surface for which they are formulated, the delivery compositions do not cause substantial, if any, physiological responses (such as inflammation or irritation) that would render the use of the delivery compositions unsuitable for topical application.

The delivery compositions of the invention include an amount of the sphingosine-1-phosphate receptor agonist active agent included in a topical delivery vehicle component. The delivery vehicle component refers to that portion of the delivery composition that is not the sphingosine-1-phosphate receptor agonist active agent.

The delivery vehicle component of the topical formulations of the invention may vary, as desired, where the particular ingredients of a given delivery vehicle component will depend, at least in part, on the nature of the particular composition. Delivery compositions of interest include liquid formulations, such as lotions (liquids containing insoluble material in the form of a suspension or emulsion, intended for external application, including metered dose or drops, spray lotions, etc.) and solutions, semi-solid formulations, such as gels (colloids in which the disperse phase has combined with the dispersion medium to produce a semisolid material, such as a jelly), foam, creams (soft solids or thick liquids) and ointments (soft, unctuous preparations), liniment or balm, oil, paste, colloidion, etc., and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols, sticks, and patches. Formulations of interest may include one or more suitable excipients, where excipients that may find use in a given formulation include, but are not limited to, those described in: Loyd, V. Allen, Remington: The Science and Practice of Pharmacy, Twenty-first Ed., (Pharmaceutical Press, 2005); Lieberman, H. A, Lachman, L. and Schwartz, J. B., Eds., Pharmaceutical Dosage Forms, Vol 1-3 Taylor & Francis, 1990; and R. I. Mahato, Ansel's Pharmaceutical Dosage Forms and Drug Delivery Systems, 2nd Ed. (Taylor & Francis, 2012), L. H. Kircik and J. B. Bikowski, Practical Dermatology (Suppl. January 2012), pp. 3-18.

Of interest in certain embodiments are topical patches. Topical patches are topical formulations that are configured to locally or transdermally deliver an active agent to a subject when topically applied to a skin surface of a subject. The formulations may include two or more layers, where the two or more layers may include at least an adhesive matrix and a backing. In certain embodiments, the two or more layers are configured to provide for extended delivery of a therapeutically effective amount of a sphingosine-1-phosphate receptor agonist active agent to a subject when the formulation is topically applied to the subject.

By "extended delivery" is meant that the topical patch is formulated to provide a therapeutically effective amount of the active agent to a subject when the topical patch is applied to a skin site of a subject for an extended period of time (e.g., a multi-day period of time). For example, the extended period of time may be a period of time that is 1 day or longer (i.e., 24 hours or longer), such as 2 days or longer (i.e., 48 hours or longer), e.g., 3 days or longer (i.e., 72 hours or longer), such as 4 days or longer (i.e., 96 hours or longer), or 5 days or longer (i.e., 120 hours or longer), including 6 days or longer (i.e., 144 hours or longer), or 7 days or longer (i.e., 168 hours or longer), such as 8 days or longer (i.e., 192 hours or longer), or 9 days or longer (i.e., 216 hours or longer), or 10 days or longer (i.e., 240 hours or longer), or 14 days or longer (i.e., 336 hours or longer), where an upper bound in some instances of any of the above ranges is 20 days, such as 18 days, e.g., 15 days, including 14 days, such as 12 days, e.g., 10 days or 9 days, e.g., 7 days. In some instances, the extended period of time is 2 to 8 days, such as 2 to 7 days, e.g., 3 to 7 days. By "therapeutically effective amount" is meant that the formulations, when applied to a skin site of a subject during its intended time of application, e.g., within 7 days of application, provides for a systemic amount of active agent that provides a desired therapeutic activity, e.g., at least relief from one or more symptoms of the disease being treated.

In certain embodiments, the formulations provide delivery of a target dosage of active agent that is 0.0001 mg/day or greater over an extended period of time (e.g., an extended period of time as described above), e.g., 0.001 mg/day or greater, over an extended period of time, 0.005 mg/day or greater, over an extended period of time, 0.01 mg/day or greater, over an extended period of time, 0.05 mg/day or greater, over an extended period of time, 0.1 mg/day or greater, over an extended period of time, 0.25 mg/day or greater, over an extended period of time, including 0.5 mg/day or greater over an extended period of time, such as 1.5 mg/day or greater over an extended period of time, or 2 mg/day or greater over an extended period of time, or 2.5 mg/day or greater over an extended period of time, or 3 mg/day or greater over an extended period of time, or 3.5 mg/day or greater over an extended period of time, or 4 mg/day or greater over an extended period of time, or 4.5 mg/day or greater over an extended period of time, or 5 mg/day or greater over an extended period of time, or 5.5 mg/day or greater over an extended period of time, or 6 mg/day or greater over an extended period of time, or 6.5 mg/day or greater over an extended period of time, or 7 mg/day or greater over an extended period of time, or 7.5 mg/day or greater over an extended period of time, or 8 mg/day or greater over an extended period of time, or 8.5 mg/day or greater over an extended period of time, or 9 mg/day or greater over an extended period of time, or 9.5 mg/day or greater over an extended period of time, or 10 mg/day or greater over an extended period of time, or 10.5 mg/day or greater over an extended period of time, or 11 mg/day or greater over an extended period of time, or 11.5 mg/day or greater over an extended period of time, or 12 mg/day or greater over an extended period of time, or 12.5 mg/day or greater over an extended period of time, or 13 mg/day or greater over an extended period of time, or 13.5 mg/day or greater over an extended period of time, or 14 mg/day or greater over an extended period of time, or 14.5 mg/day or greater over an extended period of time, or 15 mg/day or greater over an extended period of time, where an upper bound to these ranges may be 25 mg/day or less, such as 20 mg/day or less. In some instances, the formulations are configured to provide a daily dosage of 0.0001 to 5.0 mg/day, such as 0.001 to 5.0 mg/day, including 0.01 to 5.0 mg/day, including 0.1 to 5.0, such as 0.15 to 3.0 mg/day for a period of time of 3 days or longer, e.g., 3 to 7 days.

For example, the formulations may be configured to deliver a daily dosage of active agent that ranges from 0.0001 mg to 5 mg for 1 day or longer, such as 0.0001 mg to 5 mg for 2 days or longer, including 0.0001 mg to 5 mg for 3 days or longer, or 0.0001 mg to 5 mg for 5 days or longer, including 0.0001 mg to 5 mg for 7 days or longer, such as 0.0001 mg to 5 mg for 10 days or longer, or 0.0001 mg to 5 mg for 14 days or longer, where an upper bound in some instances of any of the above ranges is 20 days, such as 18 days, e.g., 15 days, including 14 days, such as 12 days, e.g., 10 days or 9 days. The extended period of time over which delivery of a therapeutically effective amount of the active agent to a subject is observed may vary, and in some instances is 1 day or longer (i.e., 24 hours or longer), such as 2 days or longer (i.e., 48 hours or longer), including 3 days or longer (i.e., 72 hours or longer), e.g., 4 days or longer (i.e., 96 hours or longer), or 5 days or longer (i.e., 120 hours or longer), or 6 days or longer (i.e., 144 hours or longer), or 7 days or longer (i.e., 168 hours or longer), or 8 days or longer (i.e., 192 hours or longer), or 9 days or longer (i.e., 216 hours or longer), or 10 days or longer (i.e., 240 hours or longer), or 14 days or longer (i.e., 336 hours or longer), where an upper bound in some instances of any of the above ranges is 20 days, such as 18 days, e.g., 15 days, including 14 days, such as 12 days, e.g., 10 days or 9 days.

For systemic delivery applications, in some instances the formulation is configured to deliver a dosage of active agent ranging from 0.1 to 5 mg/day, such as 0.15 to 2 mg/day, including 0.2 to 1 mg/day, e.g., 0.25 to 0.5 mg/day, over a given duration, where the duration may, in some instances, range from 2 to 15 days, e.g., 3 to 14 days, including 3 to 10 days, such as 3 to 7 days.

For local delivery applications, the local dose can be lower than systemic dose, i.e., the local dose for a restricted area of skin can be 10 to 10,000 fold, such as 10 to 100 fold less than the systemic dose that might delivered using the same target area of skin. In yet other embodiments, if the local delivery site is a relatively larger area, the delivered dose may be proportional to the area. For example, if the local dose is 0.1 mg/cm$^2$, the dose to treat the large area of 2000 cm² may be 200 mg. The duration for local can be multiple times a day. For local delivery applications, in some instances the formulation is configured to deliver a dosage of active agent ranging from 0.0001 to 5 mg/day, such as 0.001 to 2 mg/day, including 0.005 to 1 mg/day, e.g., 0.01 to 0.5 mg/day, over a given duration, where the duration may, in some instances, range from 2 to 15 days, e.g., 3 to 14 days, including 3 to 10 days, such as 3 to 7 days.

While the actual flux may vary, in some instances (e.g., as determined using the skin permeation assay reported in the Examples Section below) skin permeation rates of 0.05 µg/cm²/hr or greater, such as 0.1 µg/cm²/hr or greater, including 0.2 µg/cm²/hr or greater, or 0.3 µg/cm²/hr or greater, or 0.4 µg/cm²/hr or greater, or 0.5 µg/cm²/hr or greater, or 0.6 µg/cm²/hr or greater, or 0.7 µg/cm²/hr or greater, or 0.8 µg/cm²/hr or greater, or 0.9 µg/cm²/hr or greater, or 1.0 µg/cm²/hr or greater, or 1.1 µg/cm²/hr or greater, or 1.2 µg/cm²/hr or greater, or 1.3 µg/cm²/hr or greater, or 1.4 µg/cm²/hr or greater, or 1.5 µg/cm²/hr or greater, or 1.6 µg/cm²/hr or greater, or 1.7 µg/cm²/hr or greater, or 1.8 µg/cm²/hr or greater, or 1.9 µg/cm²/hr or greater, or 2.0 µg/cm²/hr or greater are provided by the formulation when the formulation is applied to a skin site of a subject for an extended period of time, where an upper bound to any of these ranges may be 5 µg/cm²/hr or less, such as 4 µg/cm²/hr or less, e.g., 3 µg/cm²/hr, including 2 µg/cm²/hr. For instance, the topical formulation may be configured to exhibit a flux of the active agent of 0.05 µg/cm²/hr or greater for 1 day or longer, such as 0.05 µg/cm²/hr or greater for 2 days or longer, including 0.05 µg/cm²/hr or greater for 3 days or longer, or 0.05 µg/cm²/hr or greater for 5 days or longer, including 0.05 µg/cm²/hr or greater for 7 days or longer, such as 0.05 µg/cm²/hr or greater for 10 days or longer, or 0.05 µg/cm²/hr or greater for 14 days or longer. The flux of the active agent may vary over the extended time period the formulation is applied to the skin site of the subject and may have skin permeation rates as described above. In some instances where the formulation is configured for systemic delivery, the formulation is configured to provide a flux ranging from 0.05 to 5 µg/cm²/hr, such as 0.08 to 4 µg/cm²/hr, including 0.1 to 3.0 µg/cm²/hr, e.g., 0.2 to 2.0 µg/cm²/hr for a period of time ranging from 2 to 15 days, such as 3 to 14 days, e.g., 3 to 10 days, including 3 to 7 days. In some instances where the formulation is configured for local delivery, the formulation is configured to provide a flux ranging from 0.05 to 5 µg/cm²/hr, such as 0.08 to 4 µg/cm²/hr, including 0.1 to 3.0 µg/cm²/hr, e.g., 0.2 to 2.0 µg/cm²/hr for a period of time ranging from 2 to 15 days, such as 3 to 14 days, e.g., 3 to 10 days, including 3 to 7 days.

In certain embodiments, the topical patch formulations are formulated to provide a cumulative delivered amount (also referred to herein as cumulative flux) of the active agent to a subject when the formulation is applied to a skin site of a subject for an extended period of time as described above. In some instances, over the extended period of time, the transdermal formulations are configured to provide a cumulative delivered amount of the active agent of 1 µg/cm² or greater, such as 100 µg/cm² or greater, including 150 µg/cm² or greater, or 200 µg/cm² or greater, or 250 µg/cm² or greater, or 300 µg/cm² or greater, or 350 µg/cm² or greater, or 400 µg/cm² or greater, or 450 µg/cm² or greater, or 500 µg/cm² or greater, or 550 µg/cm² or greater, or 600 µg/cm² or greater, or 650 µg/cm² or greater, or 700 µg/cm² or greater, or 750 µg/cm² or greater, or 800 µg/cm² or greater, or 850 µg/cm² or greater, or 900 µg/cm² or greater, or 950 µg/cm² or greater, or 1000 µg/cm² or greater. In some instances where systemic delivery is provided, the transdermal formulations are configured to provide a cumulative delivered amount of 2.4 to 1800 µg/cm², such as 5.75 to 1350 µg/cm², including 7.0 to 720 µg/cm², e.g., 10 to 350 µg/cm² for a period of time ranging from 2 to 15 days, such as 3 to 14 days, including 3 to 10 days, e.g., 3 to 7 days. In some instances where local delivery is provided, the transdermal formulations are configured to provide a cumulative flux of 2.4 to 1800 µg/cm², such as 5.75 to 1350 µg/cm², including 7.0 to 720 µg/cm², e.g., 10 to 350 µg/cm² for a period of time ranging from 2 to 15 days, such as 3 to 14 days, including 3 to 10 days, e.g., 3 to 7 days.

In some instances, the formulations are configured to provide a therapeutic daily dosage (e.g., as described above) to the subject within 24 hours or less, such as 18 hours less, including 12 hours or less, as measured from the time of application of the formulation to the subject. In such instances, the amount of active agent delivered to the subject from the formulation in the 24 hour period measured from the time of application may, in certain embodiments, range from 0.1 to 5.0, such as 0.15 to 3.0, including 0.2 to 2.0 mg/day. In certain instances, the active agent flux in the 24 hour period measured from the time of application may, in certain embodiments, range from 0.05 to 2.0, such as 0.08 to 1.5 µg/cm²/hr. In some instances, the flux observed during the first 24 hours following application of the formulation to a topical location is less than that observed during the next 24 hour period, e.g., by an amount of 5% or more, such as 10% or more, including 20% or more. In these instances, the formulations may be configured to provide for local delivery of the active agent, since the active agent remains in the local area of the region of application.

The size (i.e., area) of the patch formulations may vary, but is within a range sufficient to provide for the desired extended delivery of a therapeutically effective amount of the active agent to the subject. In certain embodiments, the size of the formulation is chosen in view of the desired transdermal flux rate of the active agent and the target dosage. For example, if the transdermal flux is 0.5 µg/cm²/hr and the target dosage is 0.5 mg/day, then the transdermal formulation may be configured to have an area of about 40 cm². Or for example, if the transdermal flux is 0.5 µg/cm²/hr and the target dosage is 1 mg/day, then the transdermal patch may be configured to have an area of about 80 cm². In certain embodiments, the formulations have dimensions such that the formulations have an area that ranges from 2 cm² to 200 cm², such as 4 cm² to 150 cm², including 5 cm² to 100 cm², or 10 cm² to 80 cm², or 10 cm² to 60 cm². In some cases, the transdermal formulations have an area of 20 to 40 cm².

The active agent layer (e.g., adhesive matrix layer) of the formulations may vary in thickness. In some embodiments, the formulations have a thickness within a range sufficient to provide for the desired extended delivery of a therapeutically effective amount of the active agent to the subject. In certain embodiments, the thickness of the formulation is chosen in view of the desired transdermal delivery rate of the active agent and the target dosage. In some instances, the thickness of the active agent layer ranges from 10 µm to 500 µm, such as 10 µm to 400 µm, including 10 µm to 300 µm, or 10 µm to 250 µm, or 10 µm to 200 µm, or 20 µm to 200 µm, or 20 µm to 150 µm, or 30 µm to 150 µm, or 40 µm to 150 µm, or 40 µm to 125 µm. In certain cases, the active agent layer has a thickness of 50 µm to 120 µm.

In some embodiments, the active agent layer is substantially insoluble in water. By insoluble in water is meant that that the layer may be immersed in fixed volume of water (e.g., 500 times the weight of the active agent layer) for a period of 1 day or longer, such as 3 days or longer, including 1 week or longer, or 2 weeks or longer, or 1 month or longer, such as 1 day to 6 months, e.g., 1 week to 3 months, including 1 week to 1 month (such as 1 week), and exhibit no significant dissolution, e.g., substantially no observable dissolution, e.g., 0.2% or less dissolution, such as 0.1% or less dissolution.

An aspect of the topical patch formulations according to embodiments of the present disclosure is that they are storage stable. By storage-stable is meant that the formulations may be stored for extended periods of time without significant degradation and/or significant reduction in activity of the active agent. In certain embodiments, the formulations are stable for 6 months or longer, such as 1 year or longer, including 2 years or longer, e.g., 3 years or longer, etc., when maintained at 25° C. under sterile conditions. In some cases, the ratio of the amount of active in the formulation after storage to the initial amount of active agent in the formulation at about 60° C. for at least one month is 90% or more, such as 91% or more, including 92% or more, or 93% or more, such as 94% or more, including 95% or more, or greater.

FIG. 1 shows a cross-section of an embodiment of a topical patch according to an embodiment of the invention. In some embodiments, the formulations include an active agent layer 2, a backing layer 1 and release liner 3, e.g., as shown in FIG. 1. Each of these layers is now described in greater detail.

Active Agent Layer

As reviewed above, transdermal formulations described herein include an active agent layer. By "active agent" is meant a chemical compound that induces a desired pharmacological or physiological effect, and include agents that are therapeutically effective or prophylactically effective. The term "active agent" also includes pharmaceutically acceptable derivatives and analogs of the active agent including, but not limited to, salts, esters, amides, prodrugs, active metabolites, analogs, polymorphs, solvates, hydrates, and the like. In some instances, the active agent layer includes one active agent (i.e., a single active agent). Active agent layers of interest include an amount of an active agent component present in a matrix, such as an adhesive matrix. The active agent component may include one or more sphingosine-1-phosphate receptor agonists, e.g., as described above.

The amount of active agent present in the active agent layer may vary. In some instances, the amount of active agent may range from 0.3 mg to 3 g, such as 0.8 mg to 2 g, including 1 mg to 1 g, e.g., 2 mg to 750 mg, including 3 mg to 500 mg. In some instances, the weight % of the active agent in the active agent layer (e.g., the adhesive matrix layer) ranges from 0.01% to 25%, such as 0.2% to 20%, including 0.3% to 15%. For example, the weight % of the active agent in the adhesive matrix may be 0.05% or more, such as 0.1% or more, including 0.5% or more, or 1% or more, or 2% or more, where in such instances the weight % may be 10% or less, e.g., 7.5% or less, including 5% or less. In certain embodiments, the weight % of the active agent ranges from 0.05 to 10% by weight of the adhesive matrix.

As summarized above, the active agent layer includes one or more active agents. As such, the sphingosine-1-phosphate receptor agonist active agent may be the only active agent present in the formulation. In these embodiments, the formulation is substantially free of other active agents. For example, as described above, the active agent may be fingolimod, and in these instances, fingolimod may be the only active agent present in the formulation. In other embodiments, the active agent layer may include two or more active agents. In some cases, the active agent layer includes two active agents, or three active agents, or four active agents, or five active agents or more. For instance, the active agent layer may include two active agents, such as a first active agent and a second active agent. In embodiments that include two or more active agents, one of the active agents is a sphingosine-1-phosphate receptor agonist (e.g., fingolimod), such as described above.

As summarized above, the active agent layer includes an amount of active agent in a matrix. In certain embodiments, the matrix is an adhesive matrix. The matrix may include polymeric materials. Suitable polymers for the adhesive matrix include, but are not limited to: polyurethanes, acrylates, styrenic block copolymers, silicones, and the like. For example, the adhesive matrix may include, but is not limited to, an acrylate polymer, polysiloxanes, polyisobutylene (PIB), polyisoprene, polybutadiene, styrenic block polymers, combinations of thereof, and the like.

Suitable styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof.

Where desired (e.g., in configurations where the formulation is configured such that, during use, the active agent layer contacts the skin), the active agent layer (e.g., the adhesive matrix) may include a pressure sensitive adhesive. The terms "pressure sensitive adhesive", "self-adhesive", and "self-stick adhesive" mean an adhesive that forms an adhesive bond when pressure is applied to adhere the adhesive with a surface. In some instances, the adhesive is one in which no solvent, water, or heat is needed to activate the adhesive. In certain embodiments of pressure sensitive adhesives, the degree of bond strength is proportional to the amount of pressure that is used to apply the adhesive to the surface.

Pressure sensitive adhesives of the adhesive matrix include, but are not limited to, acrylate polymers. Acrylate polymers may include copolymers of various monomers which may be "soft" monomers or "hard" monomers or combinations thereof. Soft monomers are characterized by having a relatively lower glass transition temperature ($T_g$), and include examples such as, but not limited to, n-butyl acrylate, 2-ethylhexyl acrylate and isooctyl acrylate. Hard monomers are characterized by having a relatively higher $T_g$, and include examples, such as, but not limited to include styrene, methyl methacrylate, ethyl acrylate and methyl acrylate. The acrylate polymers can be composed of a copolymer including bipolymer (e.g., made with two monomers), a terpolymer (e.g., made with three monomers), or a tetrapolymer (e.g., made with four monomers), or copolymers made from greater numbers of monomers. The acrylate polymers can include cross-linked and non-cross-linked polymers. The polymers can be cross-linked by cross-linking agents to provide the desired cross-linked polymers.

Monomers from which the acrylate polymers are produced include at least two or more components selected from acrylic acids, alkyl acrylates, methacrylates, copolymerizable secondary monomers or monomers with functional groups, and the like. Monomers (e.g., "soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference. Acrylic adhesives, available from several commercial sources, are sold under the trade names AROSET, DUROTAK, EUDRAGIT, GELVA, and NEOCRYL.

In some embodiments, the active agent adhesive layer may include a pressure sensitive adhesive which is a formulation that is, or is substantially the same as, a formulation selected from the group consisting of: DuroTak® 87-9301 (Henkel), DuroTak® 87-900A (Henkel), and the like. The term "substantially the same" as used herein refers to a formulation that is an acrylate polymer in an organic solvent solution and provides for the functionality as described herein. The active agent layer may include a single pressure sensitive adhesive, or a combination of two or more pressure sensitive adhesives. In some instances, the pressure sensitive adhesive may make up from 10% to 95%, such as 20% to 90%, including 20% to 80%, or 20% to 70%, or 30% to 70%, or 30% to 60% by weight of the adhesive matrix.

Permeation Enhancer

In certain embodiments, the active agent layer includes a permeation enhancer. The permeation enhancer may facilitate the absorption of the active agent by the skin of the subject. The permeation enhancer may also be referred to as a percutaneous absorption enhancer.

The permeation enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —OCH$_2$CH$_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of permeation enhancers include, but are not limited to lactic acid, tartaric acid, 1,2,6-hexanetriol, benzyl alcohol, lanoline, potassium hydroxide (KOH), and tris(hydroxymethyl)aminomethane. Specific examples of permeation enhancers include, but are not limited to glycerol monooleate (GMO) and sorbitan monolaurate (SML), lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol, alone or in combinations of one or more. Of interest are permeation enhancers that are tailored to enhance permeation of surfactant type active agents. Examples of such permeation enhances include combinations of semi-polar solvents, e.g., propylene glycol, butane diol, N-methylpyrrolidone, dimethyl sulfoxide, diethylene glycol methyl ether, and dimethyl isosorbide, etc., and surfactants, such as isopropyl myristate, oleic acid, lauryl lactate, etc.

In some cases, the adhesive matrix contains the permeation enhancer in an amount ranging from 1% to 25% (w/w), such as from 1% to 20% (w/w), and including from 1% to 15% (w/w), or 1% to 10% (w/w). In certain cases, the adhesive matrix contains the permeation enhancer in an amount of 3% (w/w), or 5% (w/w), or 7% (w/w), or 9% (w/w).

Additional Components

In some embodiments, the polymer matrix includes a PVP. The term "PVP or "polyvinylpyrrolidone" refers to a polymer, either a homopolymer or copolymer, containing N-vinylpyrrolidone as the monomeric unit. PVP polymers may be homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. The amount and type of soluble PVP used may vary. In some instances, the PVP is present in an amount from 1% to about 40% by weight, such as from 1% to about 20% by weight, based on the total weight of the polymer matrix. In some instances, the PVP has a molecular weight of 2,000 to 1,100,000 Daltons, including 5,000 to 100,000 Daltons, and 7,000 to 54,000 Daltons. The polymer may be crosslinked, such as for example crosslinked polyvinylpyrrolidone (PVP-CLM). Polyvinylpyrrolidone, such as PVP-CLM, PVP K17, PVP K30, PVP K90, that inhibit drug crystallization, have hygroscopic properties that improve the duration of wear, and improve the physical properties, e.g., cold flow, tack, cohesive strength, of the adhesive.

In certain embodiments, compositions may include a non-volatile solvent (i.e., a solvent that is non-volatile as compared to acetone, isopropanol or water, but may nonetheless exhibit some volatility), such as dimethyl sulfoxide (DMSO), N-methylpyrrolidone, dimethyl isosorbide, propylene glycol, hexylene glycol and benzyl alcohol. The non-volatile solvent may be present in a composition in an amount of between 1% and about 30%, such as 2 to 20% and including 3 to 15% by weight of the composition.

The topical patches may optionally include one or more antioxidants, such as but not limited to: tocopherol and derivatives, e.g., tocopherol acetate or tocopherol polyethylene glycol succinate, ascorbic acid and derivatives, e.g., ascorbyl palmitate, butylated hydroxyanisole, butylated hydroxytoluene, fumaric acid, malic acid, propyl gallate, metabisulfates and derivatives, etc. The antioxidant may be present in any convenient amount, ranging in some instances from 0.001 to 5.0% w/w of the formulation.

Where desired, the composition may further include one or more fillers. Fillers of interest include, but are not limited to: metal oxides (such as zinc oxide and titanium oxide), metal salts (such as calcium carbonate, magnesium carbonate and zinc stearate), silicic acid compounds (such as kaolin, talc, bentonite, Aerosil, hydrous silica, aluminum silicate, magnesium silicate and magnesium aluminometasilicate) and metal hydroxides (such as aluminum hydroxide). Where present, such fillers may be 1 to 75%, such as 2 to 50% by weight of the adhesive matrix component.

Multi-Layer Structure

As summarized above, the transdermal formulations described herein have a multi-layer structure. By multi-layer structure is meant that the formulations include two or more distinct layers, where the total number of distinct layers in the formulation may be two or more, such as 3 or more, including 4 or more, e.g., 5 or more. In some instances, the number of distinct layers may range from 2 to 5, such as from 2 to 4, including 2 or 3 layers. For example, the transdermal formulation may have an adhesive matrix and a backing. As described herein, the thicknesses of each of the layers in the formulation may be the same or different, as desired.

Backing

As summarized above, the transdermal formulation may include a backing (e.g., support layer). The backing may be flexible to an extent that it can be brought into close contact with a desired topical location of a subject. The backing may be fabricated from a material that does not absorb the active agent, and does not allow the active agent to be released from the backing side of the transdermal formulation. Backing materials of interest may be occlusive (i.e., impermeable), semi-occlusive or breathable (permeable). The backing may include, but is not limited to, non-woven fabrics, woven fabrics, films (including sheets), foils, porous bodies, foamed bodies, paper, composite materials obtained by laminating a film on a non-woven fabric or fabric, and combinations thereof.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene (including low density and high density polyethylene (LDPE, HDPE) and polypropylene; polyacrylic resins such as polymethyl methacrylate and polyethyl methacrylate; polyester resins such as polyethylene terephthalate, poly-chloro-tri-fluoro-ethylene, acrylonitrile methyl acrylate copolymer, polybutylene terephthalate and polyethylene naphthalate; and polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Foils of interest include metallic foils, e.g., aluminum foils, etc. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric. In certain embodiments, the backing includes a polyester, such as polyethylene terephthalate (PET).

The size of the backing may vary, and in some instances the backing is sized to cover the desired topical target site. In some embodiments, the backing has a length ranging from 2 to 100 cm, such as 4 to 50 cm and a width ranging from 2 to 100 cm, such as 4 to 50 cm.

In some embodiments, the backing layer is insoluble in water. By insoluble in water is meant that that the backing layer may be immersed in water for a period of 1 day or longer, or 3 days or longer, or 5 days or longer, such as 1 week or longer, or 2 weeks or longer, including 1 month or longer, and exhibit little if any dissolution, e.g., no observable dissolution.

The backing layer may be in contact with a surface of the active agent layer. For example, where the formulation is configured so that one surface of the active agent layer contacts the skin upon application, the backing will be in contact with an opposing surface of the active agent layer.

Release Liner

In some embodiments, a release liner is provided on the active agent layer (i.e., the adhesive matrix), and specifically on a surface of the active agent layer that is distal (i.e., opposite) from the backing layer. The release liner may facilitate the protection of the active agent layer before use of the transdermal formulation. In certain cases, the release liner is configured to be removable from the adhesive matrix without retaining the adhesive matrix on the release liner.

The release liner may be any convenient material, where representative release liners include polyesters, such as polyethylene terephthalate, polypropylene, and the like. In certain embodiments, the release liner includes a coated substrate, which, for example, may be prepared by treating one side of polyethylene-coated wood free paper, polyolefin-coated glassine paper, a polyethylene terephthalate (polyester) film, a polypropylene film, or the like with a silicone treatment. In certain instances, the release liner includes a polyester film with a silicone treatment.

Adhesive Overlay

Optionally, an adhesive overlay can be used to increase the adhesion of the composition when applied to the skin. Adhesive overlays can include a layer of adhesive present on a backing material, such as a porous, non-porous, occlusive, or breathable backing material. The dimensions of the adhesive overlay are chosen to provide the desired functionality, where in some instances the dimensions are chose such that the adhesive overlay, when applied over the active agent formulation, extends some distance beyond one or more of the sides of the active agent formulation. In some instances, the area of the adhesive overlay exceeds the area of the active agent formulation by 5% or more, such as by 10% or more, including by 20% or more. During use, the adhesive overlay can be applied by the patients, by the care givers, or can be integrated in the kits.

Fabrication Methods

Aspects of the present disclosure also include methods of producing the topical compositions, such as topical patches, e.g., as described above. In certain embodiments, the method includes mixing an active agent layer precursor composition with a sphingosine-1-phosphate receptor agonist to produce an active agent layer-sphingosine-1-phosphate receptor agonist mixture. In some cases, the active agent layer precursor composition is an adhesive matrix, and as such, the method includes mixing an adhesive matrix with the sphingosine-1-phosphate receptor agonist to produce an adhesive matrix-sphingosine-1-phosphate receptor agonist mixture. In certain instances, the method further includes applying the adhesive matrix-sphingosine-1-phosphate receptor agonist mixture to a backing. The method may further include applying a release liner to the adhesive matrix on the side of the adhesive matrix opposite the backing. In certain cases, the adhesive matrix-sphingosine-1-phosphate receptor agonist mixture may be applied to the backing first, followed by application of the release liner. In other embodiments, the adhesive matrix-sphingosine-1-phosphate receptor agonist mixture is applied to the release liner first and then followed by application of the backing. In certain instances, the method of producing the transdermal formulation further includes placing the transdermal formulation into a package. After placing the transdermal formulation into the package, the method may include sealing the package.

Gel Formulations

As mentioned above, other topical formulations of interest are gel formulations. In gel formulations, the amount of active agent present in the gel formulation (i.e., gel composition) may vary. In some instances, the weight % of the active agent in the gel composition ranges from 0.01% to 25%, such as 0.2% to 20%, including 0.25% to 15%. For example, the weight % of the active agent in the gel composition may be 0.05% or more, such as 0.1% or more, including 0.25% or more, or 5% or more, or 0.75%, e.g., 1% or more, 2% or more, where in such instances the weight % may be 10% or less, e.g., 7.5% or less, including 5% or less. In certain embodiments, the weight % of the active agent ranges from 0.25 to 2% by weight of the gel composition.

In addition to the active agent, gel formulations include a gel delivery vehicle component, where the gel delivery vehicle may be an aqueous or non-aqueous gel delivery vehicle. Aqueous gel delivery vehicles (i.e., hydrogel delivery vehicles) of interest are vehicles that include, in addition to the active agent, at least a water-soluble high molecular weight substance, e.g., a water-soluble polymer gel and water. Water-soluble high molecular weight substances of interest include water-soluble polymers, where polymers of interest include, but are not limited to: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabic gum, acacia, tragacanth gum, karaya gum, and starch acrylate copolymer or other starch sodium acrylate graft copolymers. Metallic salts of these, as well as the products of cross-linking these by means of organic or inorganic cross-linking agents, are also of interest. Specifically, cross-linking agents may be included in the subject hydrogel compositions, where exemplary cross linking agents include, but are not limited to: dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride. These water-soluble polymers can be used to bring out the properties and characteristics of the other starting materials used in the hydrogel composition, and in practice can be used alone or in combinations of 2 or more. The amount of water soluble high molecular weight substance(s) present in the adhesive gel may vary, and in some instances ranges from 0.5 to 20% (w/w), such as 2 to 15% (w/w) and the amount of cross-linking agent, if present, may range in some instances from 0.01 to 2% (w/w), such as from 0.02 to 1.5% (w/w) and including from 0.03 to 1% (w/w).

While any convenient water may be employed as the water component, of interest are distilled water or ion-exchange water or the like, which is preferred in many embodiments of the subject invention. The amount of water present in the hydrogel vehicle composition is sufficient to impart the desired physical properties to the hydrogel composition. The amount of water will vary depending on the particular high molecular weight substance(s) employed, where the amount of water in the hydrogel composition may, in some instances, be 25% or more water by weight, such as 30% or more water (w/w). For example, the amount of water may range from 25% to 90%, such as from 20% to 80%, and including from 30% to 50%.

Where desired, the gel delivery vehicle may further include a water-retaining agent. The water-retaining agent or water-holding agent is any agent that is capable of at least diminishing the volatilization of water contained in the composition so that the water content in the composition base is maintained at least a substantially constant, if not constant, level during storage and use of the composition. One or more water-retaining agents may be employed in the compositions, where the amount of water-retaining agent present in the composition may, in some instances, range from 1 to 40%, such as from 3 to 30% by weight. Examples of suitable water-retaining or water-holding agents include, but are not limited to: 1 or more types of polyvalent or polyhydric or sugars or alcohols, such as glycerin, erythritol, sorbitol, propylene glycol, diethylene glycol, 1,3-butylene glycol, and ethylene glycol, and the like.

In addition to the aforementioned ingredients, various additives that are used in ordinary topical preparations may also be suitably compounded as needed, including inorganic substances such as kaolin, bentonite, and titanium dioxide; preservatives such as paraben; anionic, cationic, and non-ionic surfactants; metallic aluminum crosslinking agents such as aluminum chloride, dried aluminum hydroxide gel, and dihydroxyaluminum aminoacetate; oils such as jojoba oil and castor oil; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents. The pH of the compositions typically is one that lies in a physiologically acceptable range, where the pH may in some instances from 3.0 to 8.0, such as from 4.0 to 7.0.

In certain embodiments, the formulations provide delivery of a target dosage of active agent that is 0.0001 mg/day or greater over an extended period of time (e.g., an extended period of time as described above), e.g., 0.001 mg/day or greater, over an extended period of time, including 0.005 mg/day or greater over an extended period of time, such as 0.01 mg/day or greater over an extended period of time, or 2 mg/day or greater over an extended period of time, or 2.5 mg/day or greater over an extended period of time, or 3 mg/day or greater over an extended period of time, or 3.5 mg/day or greater over an extended period of time, or 4 mg/day or greater over an extended period of time, or 4.5 mg/day or greater over an extended period of time, or 5 mg/day or greater over an extended period of time, or 5.5 mg/day or greater over an extended period of time, or 6 mg/day or greater over an extended period of time, or 6.5 mg/day or greater over an extended period of time, or 7 mg/day or greater over an extended period of time, or 7.5 mg/day or greater over an extended period of time, or 8 mg/day or greater over an extended period of time, or 8.5 mg/day or greater over an extended period of time, or 9 mg/day or greater over an extended period of time, or 9.5 mg/day or greater over an extended period of time, or 10 mg/day or greater over an extended period of time, or 10.5 mg/day or greater over an extended period of time, or 11 mg/day or greater over an extended period of time, or 11.5 mg/day or greater over an extended period of time, or 12 mg/day or greater over an extended period of time, or 12.5 mg/day or greater over an extended period of time, or 13 mg/day or greater over an extended period of time, or 13.5 mg/day or greater over an extended period of time, or 14 mg/day or greater over an extended period of time, or 14.5 mg/day or greater over an extended period of time, or 15 mg/day or greater over an extended period of time, where an upper bound to these ranges may be 25 mg/day or less, such as 20 mg/day or less, e.g., 15 mg/day, including 10 mg/day. In some instances, the formulations are configured to provide a daily dosage of 0.0001 to 10 mg/day, such as 0.001 to 5 mg/day, including 0.005 to 2 mg/day, e.g., 0.01 to 1 mg/day, for a period of time of 2 to 15 days, such as 3 to 14 days, including 3 to 10 days, e.g., 3 to 7 days.

While the actual flux may vary, in some instances skin permeation rates of 0.05 $\mu g/cm^2/hr$ or greater, such as 0.1 $\mu g/cm^2/hr$ or greater, including 0.2 $\mu g/cm^2/hr$ or greater, or 0.3 $\mu g/cm^2/hr$ or greater, or 0.4 $\mu g/cm^2/hr$ or greater, or 0.5 $\mu g/cm^2/hr$ or greater, or 0.6 $\mu g/cm^2/hr$ or greater, or 0.7 $\mu g/cm^2/hr$ or greater, or 0.8 $\mu g/cm^2/hr$ or greater, or 0.9 $\mu g/cm^2/hr$ or greater, or 1.0 $\mu g/cm^2/hr$ or greater, or 1.1 $\mu g/cm^2/hr$ or greater, or 1.2 $\mu g/cm^2/hr$ or greater, or 1.3 $\mu g/cm^2/hr$ or greater, or 1.4 $\mu g/cm^2/hr$ or greater, or 1.5 $\mu g/cm^2/hr$ or greater, or 1.6 $\mu g/cm^2/hr$ or greater, or 1.7 $\mu g/cm^2/hr$ or greater, or 1.8 $\mu g/cm^2/hr$ or greater, or 1.9 $\mu g/cm^2/hr$ or greater, or 2.0 $\mu g/cm^2/hr$ or greater are provided by the formulation when the formulation is applied to a skin site of a subject for an extended period of time, where an upper bound to any of these ranges may be 5 $\mu g/cm^2/hr$ or less, such as 4 $\mu g/cm^2/hr$ or less, e.g., 3 $\mu g/cm^2/hr$, including 2 $\mu g/cm^2/hr$. For instance, the topical formulation may be configured to exhibit a flux of the active agent of 0.05 $\mu g/cm^2/hr$ or greater for 1 day or longer, such as 0.05 $\mu g/cm^2/hr$ or greater for 2 days or longer, including 0.05 $\mu g/cm^2/hr$ or greater for 3 days or longer, or 0.05 $\mu g/cm^2/hr$ or greater for 5 days or longer, including 0.05 $\mu g/cm^2/hr$ or greater for 7 days or longer, such as 0.05 $\mu g/cm^2/hr$ or greater for 10 days or longer, or 0.05 $\mu g/cm^2/hr$ or greater for 14 days or longer. The flux of the active agent may vary over the extended time period the formulation is applied to the skin site of the subject and may have skin permeation rates as described above. In some instances, the formulation is configured to provide a flux ranging from 0.05 to 5 $\mu g/cm^2/hr$, such as 0.08 to 4 $\mu g/cm^2/hr$, including 0.1 to 3.0 $\mu g/cm^2/hr$, e.g., 0.2 to 2.0 $\mu g/cm^2/hr$ for a period of time ranging from 2 to 15 days, such as 3 to 14 days, e.g., 3 to 10 days, including 3 to 7 days.

In certain embodiments, the formulations are formulated to provide a cumulative delivered amount (also referred to herein as cumulative flux) of the active agent to a subject when the formulation is applied to a skin site of a subject for an extended period of time as described above. In some instances, over the extended period of time, the formulations are configured to provide a cumulative delivered amount of the active agent of 1 $\mu g/cm^2$ or greater, such as 100 $\mu g/cm^2$ or greater, including 150 $\mu g/cm^2$ or greater, or 200 $\mu g/cm^2$ or greater, or 250 $\mu g/cm^2$ or greater, or 300 $\mu g/cm^2$ or greater, or 350 $\mu g/cm^2$ or greater, or 400 $\mu g/cm^2$ or greater, or 450 $\mu g/cm^2$ or greater, or 500 $\mu g/cm^2$ or greater, or 550 $\mu g/cm^2$ or greater, or 600 $\mu g/cm^2$ or greater, or 650 $\mu g/cm^2$ or greater, or 700 $\mu g/cm^2$ or greater, or 750 $\mu g/cm^2$ or greater, or 800 $\mu g/cm^2$ or greater, or 850 $\mu g/cm^2$ or greater, or 900 $\mu g/cm^2$ or greater, or 950 $\mu g/cm^2$ or greater, or 1000 $\mu g/cm^2$ or greater. In some instances, the formulations are configured to provide a cumulative flux of 2.4 to 1800 $\mu g/cm^2$, such as 5.75 to 1350 $\mu g/cm^2$, including 7.0 to 720 $\mu g/cm^2$, e.g., 10 to 350 $\mu g/cm^2$ for a period of time ranging from 2 to 15 days, such as 3 to 14 days, including 3 to 10 days, e.g., 3 to 7 days.

Methods

Methods of using the topical compositions include delivering the active agent to a subject, e.g., for an extended period of time. In certain embodiments, the method includes applying to skin of the subject a topical composition, e.g., transdermal patch, as described herein, and maintaining the applied topical composition on the skin of the subject for an extended period of time to deliver the active agent to the subject for an extended period of time. As described above, where the topical composition is a topical patch, the topical composition includes an adhesive matrix, and as such, in certain instances, the formulation adheres to the skin of the subject after application without any additional components (e.g., overlays, dressings, etc.) to maintain the formulation on the skin of the subject for the extended period of time.

The active agent may be delivered to the subject for an extended period of time in a therapeutically effective amount in order to treat the subject for a target condition of interest, e.g., as described in the Utility section below. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the topical composition disclosed herein can be topically applied to a subject. For example, the topical composition may be applied to any convenient topical site (e.g., skin site). Application may include contacting an active agent layer to a skin site of the subject. Topical sites of interest include keratinized skin sites, and therefore include, but are not limited to arms, legs, torso, hips, abdomen, buttocks, etc. of the subject. The surface area that is covered by the formulation following application is sufficient to provide for the desired amount of active agent administration. For instance, where the topical composition is a topical patch, the topical patch may be configured so that the adhesive matrix contacts a skin area ranging in size from 10 $cm^2$ to 200 $cm^2$, such as 10 $cm^2$ to 150 $cm^2$, including 10 $cm^2$ to 100 $cm^2$, or 10 $cm^2$ to 80 $cm^2$, or 10 $cm^2$ to 60 $cm^2$. In some cases, the adhesive matrix contacts a skin area of 40 $cm^2$.

The topical composition may be maintained at the topical site to which it has been applied for an extended period of time, e.g., to deliver a desired amount of active agent. In some instances, the period of time that the formulation is maintained at the site of application is 1 day or longer (i.e., 24 hours or longer), such as 2 days or longer (i.e., 48 hours or longer), e.g., 3 days or longer (i.e., 72 hours or longer), such as 4 days or longer (i.e., 96 hours or longer), or 5 days or longer (i.e., 120 hours or longer), or 6 days or longer (i.e., 144 hours or longer), or 7 days or longer (i.e., 168 hours or longer), or 8 days or longer (i.e., 192 hours or longer), or 9 days or longer (i.e., 216 hours or longer), or 10 days or longer (i.e., 240 hours or longer), or 14 days or longer (i.e., 336 hours or longer). In some instances, the transdermal formulation is maintained at the site of application for a period of 2 to 8 days, such as 3 to 7 days.

In practicing the subject methods, the topical composition may be applied a single time or a plurality of times over a given time period, e.g., the course of the condition being treated, where the dosing schedule when a plurality of formulations are administered over a given time period may be daily, weekly, biweekly, monthly, etc. After the topical composition has been applied to the skin site for the desired amount of time (e.g., an amount of time sufficient to deliver a target dose of the active agent to the subject over a period of time), the composition may be removed from the skin site. A new transdermal formulation may be applied at the same or at a different skin site. For example, for transdermal delivery, a new topical composition may be applied to a different skin site to reduce the possible occurrence of skin irritation and/or skin sensitization at the prior site of application. Alternatively, for local topical delivery, a new topical composition may be applied to the same skin site. Where desired, an overlap of dosages may be employed, e.g., where a second dosage is applied while the first dosage is still applied. The period of overlap, i.e., the time during which two different dosages are applied to the skin at the same time may vary, and in some instances may be 1 hour to 48 hours, e.g., 6 hours to 36 hours, such as 12 hours to 24 hours. Even when there is no period of overlap, there may be residual active agent deposited in the stratum corneum as the site of application that keeps delivering while diffusion from the patch on a new application site approaches its maximum delivery or steady-state delivery.

Aspects of the invention include methods of topically locally or transdermally delivering a therapeutically effective amount of a sphingosine-1-phosphate receptor agonist active agent to a subject. By "therapeutically effective amount" is meant a level, e.g., in the skin or in the plasma or other internal bodily tissue or fluid, that provides for reduction, inhibition, or prevention of the symptoms or mechanisms underlying a condition to be treated, e.g., as reviewed below.

A subject delivery method will, in certain embodiments, provide a therapeutic level of sphingosine-1-phosphate receptor agonist active agent. In some embodiments, transdermal delivery will provide a therapeutic level of a sphingosine-1-phosphate receptor agonist active agent over a desired period of time, e.g. over a period of time ranging from 0.5 hour to 1 week. In certain embodiments, transdermally delivering a therapeutically effective amount of a sphingosine-1-phosphate receptor agonist active agent will provide a therapeutic level of a sphingosine-1-phosphate receptor agonist active agent over an extended period of time, where the therapeutic level of the sphingosine-1-phosphate receptor agonist active agent remains relatively constant in the individual over the extended period of time. A "relatively constant" level is a level that varies by 30% or less, e.g., 25% or less, including 20% or less, such as 15%, including 10%, e.g., 5% or less over a given period of time.

By extended period of time is meant a time of 3 hr or longer, such as 2 days or longer, e.g., a time ranging from 0.5 days to 2 weeks, such as from 1 day to 1 week.

In certain embodiments, the subject methods include a diagnostic step. Individuals may be diagnosed as being in need of the subject methods using any convenient protocol. In addition, individuals may be known to be in need of the subject methods, e.g., they are suffering from multiple sclerosis, a dermatological skin proliferative disease, etc. Diagnosis or assessment of target condition can be performed using any convenient diagnostic protocol. Methods of diagnosing multiple sclerosis include, but are not limited to, one or more of: magnetic resonance imaging protocols, which are employed to identify, characterize and sometimes date nervous system (e.g., brain) lesions; electrophysiological tests, which assesses impulses traveling through the nerves to determine if the impulses are moving normally or too slowly; and cerebro-spinal fluid assays, which assays evaluate the fluid surrounding the brain and spinal cord to identify abnormal chemicals (e.g., antibodies) or cells that suggest the presence of multiple sclerosis.

In certain embodiments, the method may further include assessing the efficacy of the treatment protocol that includes administration of the active agent (e.g., sphingosine-1-phosphate receptor agonist). Assessing the efficacy of treatment may be performed using any convenient protocol, e.g., performing one or more of the diagnostic protocols (such as described above) to determine if any improvement has occurred.

In some instances, transdermal formulations may be administered in conjunction with one or more additional therapies specific for the target condition of interest. As such, the transdermal formulations may be used alone to treat the target condition, or alternatively, may be used as an adjunct to other forms of treatment.

Parenteral administration of Fingolimod HCl for the treatment of multiple sclerosis is associated with adverse events (AEs) such as fatal viral infections, skin cancer, and macular edema in subjects to which Fingolimod HCl was orally administered. Transdermal delivery of sphingosine-1-phosphate receptor agonist active agents according to the subject methods provides more accurate control over the rate at which the sphingosine-1-phosphate receptor agonist active agent is administered to the subject. Moreover, the subject methods provide more constant systemic levels of the active agent during the administration period, thereby avoiding the substantial peak to trough fluctuations (as much as 45% for the phosphorylated (active) form of fingolimod and 20% for non-phosphorylated fingolimod) that have been observed with orally administered fingolimod HCl and which may underlie the AEs associated with this route of administration.

Accordingly, in certain aspects, the transdermal delivery methods of the invention result in reduced incidence of adverse events (e.g., viral infections, skin cancer, and/or macular edema) as compared to parenteral (e.g., oral) routes of administration of the sphingosine-1-phosphate receptor agonist active agent (e.g., fingolimod HCl). For example, the subject methods may result in a reduced incidence of adverse events such as a 5%, 10%, 15%, 20%, 25%, 50%, 75% or more reduction in the incidence of adverse events as compared to orally administered sphingosine-1-phosphate receptor agonist active agent (e.g., fingolimod HCl). Although the active agents employed herein exhibit anti-proliferative activity, topical compositions of such may be surprisingly administered topically as described herein without significant incidence of dermatological adverse events.

As reviewed in the Utility section below, methods and devices of the invention find use in the treatment of a variety of conditions, including immune system disorders, e.g., multiple sclerosis, hyperproliferative dermatological disorders, e.g., psoriasis, acne, skin cancers, etc.

In some embodiments, a subject delivery method treats an immune system disorder, e.g., the method is suitable for abortive therapy of an immune system disorder. In other embodiments, a subject delivery method prevents the occurrence of an immune system disorder. In some embodiments, a subject delivery method reduces or eliminates one or more symptoms of an immune system disorder. It will be understood that the immune system disorder may be any immune system disorder for which a sphingosine-1-phosphate receptor agonist active agent (e.g., fingolimod) is effective against, including autoimmune disorders, e.g., multiple sclerosis.

Individuals who are suitable for treatment with a subject delivery method include individuals suffering from an immune system disorder; and individuals who are prone to suffering from immune system disorders, e.g., individuals with a history of immune system disorders. Individuals who are suitable for treatment with a subject delivery method also include individuals suffering from relapsing remitting immune systems disorders, such as relapsing remitting multiple sclerosis. Individuals may be diagnosed as being in need of the subject methods using any convenient protocol, and are generally known to be in need of the subject methods prior to practicing the subject methods.

Topical compositions, e.g., as described herein, may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects (e.g., patients) are humans.

Utility

The topical composition, methods, and kits of the invention are useful in numerous contexts, including the treatment of a variety of conditions. For example, the formulations, methods, and kits find use in treating an immune system disorder in a subject. Immune systems disorders that may be treated according to the subject methods include, but are not limited to, multiple sclerosis, autoimmune encephalomyelitis, arthritis, lupus (e.g., lupus nephritis), transplant (e.g., allograft) rejection, and the like.

As set forth above, the sphingosine-1-phosphate receptor agonist active agent may be fingolimod freebase or a salt thereof, e.g., fingolimod HCl. It has been shown that fingolimod HCl is effective in treating a number of autoimmune disorders including multiple sclerosis. See, e.g., Kappos et al., Oral Fingolimod (FTY720) for Relapsing Multiple Sclerosis (2006) N. Engl. J. Med.; 355:1124-1140, and Cohen et al., Oral Fingolimod or Intramuscular Interferon for Relapsing Multiple Sclerosis (2010) N. Engl. J. Med.; 362:402-415. In certain aspects, the subject methods are methods of treating multiple sclerosis in a subject, the methods including iontophoretically delivering a therapeutically effective amount of Fingolimod HCl to the subject.

Specific applications in which methods and devices described herein may be employed include, but are not limited to: those described in U.S. Pat. Nos. 5,604,229; 5,505,715; 6,004,565 and 6,121,329, as well as Published United States Patent Application Nos. 2005/0090520; 2009/0275553; 2010/0160259; and 2010/0168078.

Applications of interest also include the treatment of hyperproliferative dermatological disorders, e.g., psoriasis, acnes, skin cancers, etc.

Kits

Kits for use in practicing certain methods described herein are also provided. In certain embodiments, the kits include one or more transdermal formulations as described above. In a given kit that includes two or more formulations, the formulations may be individually packaged or present within a common container.

In certain embodiments, the kit includes a transdermal formulation present in a sealed package. The sealed package may include a packaging material that prevents passage of moisture, oxygen and other agents, i.e., the package includes in a moisture/oxygen barrier material. Any suitable barrier material may be employed, where barrier materials of interest include metallic layers, e.g., aluminum, where in certain embodiments, the barrier layer is an aluminum layer. The barrier layer may have a thickness sufficient to provide for the barrier function, where the thickness may range from about 5 µm to 15 µm, such as from about 5 µm to 10 µm. In certain embodiments, the package is a laminate of the barrier layer in combination with one or more additional layers, e.g., polymeric layers, paper layers, etc. The various components of the kits may be present in separate containers, or some or all of them may be pre-combined. For example, in some instances, one or more components of the kit, are present in a sealed package, as a pouch, which may be sterile, e.g., a sterile foil pouch or envelope.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation.

EXAMPLES

I. Topical Patch Formulations

A. Materials and Methods

1. Preparation of Fingolimod Formulations

Fingolimod base or fingolimod hydrochloride formulations were prepared by a solvent evaporation method. The drug was dissolved in a minimum amount of organic solvent (ethanol or isopropanol) using a vortex mixer. Weighed quantities of other ingredients (if present) and the required amount of organic solvents (ethyl acetate or heptane) were added into the drug solution and mixed thoroughly. The adhesive was added into the mixture of drug and other excipients, and mixed until homogeneous. The homogeneous slurry (about 30-60% solid content) was casted onto a release liner (silicone or fluropolymer coated polyester film) and dried at 65°-80° C. for 10-90 minutes. The adhesive films were then laminated onto a PET backing, cut to the desired size, and pouched. The other ingredients used in this study are PVP CLM, Glyceryl monolaurate, Lauryl lactate, Dimethylsulfoxide, Aerosil®, PVP K30, PVP K90 or Eudragit EPO®.

2. Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm$^2$. The release liner was removed and the drug delivery system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing 0.9% sodium chloride, 1% Tween 80 and 0.01% Gentamicin was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

B. Results

1. Patch Example 1

In-Vitro Permeation of Fingolimod Obtained from Fingolimod Base Patch and Fingolimod Hydrochloride Patch To evaluate fingolimod permeation through the skin, fingolimod formulations in acrylate polymer (Duro-Tak 900A) were made. Due to the low solubility of fingolimod in the adhesive (less than 1%), polyvinyl pyrrolidone (PVP) was used as a solubility aid and inhibitor of recrystallization. The permeation of fingolimod obtained from the fingolimod HCl patch was also evaluated. To improve the skin transport of the salt form of the drug, Eudragit EPO cationic copolymer was used to form the free base of drug and thereby facilitate the permeation of drug through skin.

Figure 2:
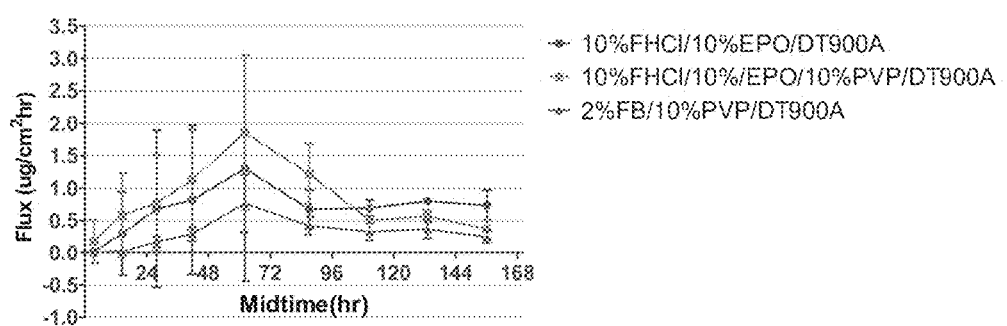
FIGS. 2, 3 and 4 provide the results of transdermal flux tests performed on various topical patch formulations, as described in greater detail in the Experimental section, below.

Using the general method described previously, fingolimod HCl (FHCl) and fingolimod base (FB) formulations containing Eudragit EPO and/or PVP K30 in Duro-Tak 900A were prepared. The details of the ingredients in each formulation are shown in Table 1. The flux through human cadaver skin was measured and the results are presented in FIG. 2. All formulations provided the permeation of fingolimod through the skin.

TABLE 1

| | % w/w | | |
|---|---|---|---|
| Ingredients | A (10% FHCl/10% EPO/DT900A) | B (10% FHCl/10% EPO/10% PVP/DT 900A) | C (2% FB/10% PVP/DT900A) |
| Fingolimod HCl | 10 | 10 | — |
| Fingolimod base | — | — | 2 |
| Eudragit EPO ® | 10 | 10 | — |
| PVP K30 | — | 10 | 10 |
| Duro-Tak 87-900A | 80 | 70 | 88 |

2. Patch Example 2

Flux of Fingolimod Obtained from Fingolimod Base Formulations Prepared with Duro-Tak 9301 Adhesive The permeation of fingolimod obtained from fingolimod formulations containing solubilizers and/or enhancers in Duro-Tak 87-9301 adhesive was evaluated. Due to the low solubility of fingolimod in adhesive (less than 1%), PVP K90 was used as solubility aid and inhibitor of recrystallization. The other ingredients, i.e., Lauryl Lactate (LL), Glyceryl monooleate (GMO), Dimethyl sulfoxide (DMSO) were used as solubilizers and enhancers. In the formulation containing a high percentage of liquid (formulation G), Aerosil (ARS) was added to increase the uniformity of the patch.

Figure 3:
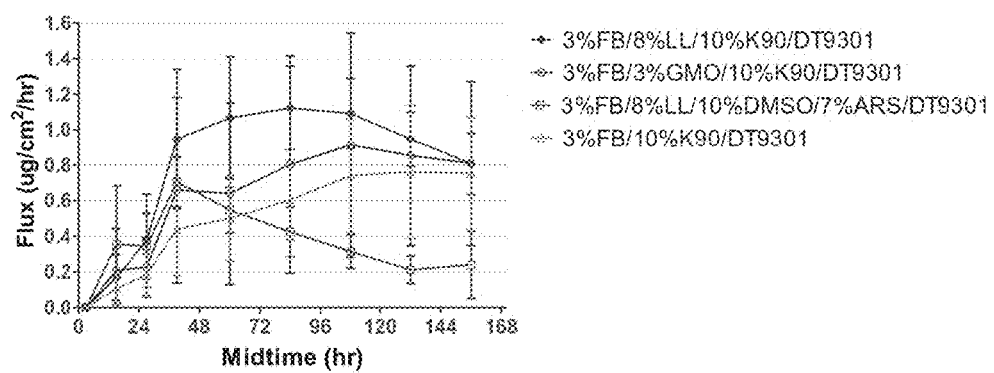

Using the general method described previously, fingolimod base formulations containing Lauryl Lactate (LL), Glyceryl monooleate (GMO), Dimethyl sulfoxide (DMSO), Aerosil® (ARS), and PVP K90 in Duro-Tak 9301 adhesive were prepared. The details of the ingredients in each formulation are shown in Table 2. The flux through human cadaver skin was measured and the results are presented in FIG. 3. LL and GMO appear to have an enhancement effect on the fingolimod flux. The formulation containing DMSO (G) shows the permeation of drug into the receptor solution earlier than the other formulations (D, E and F). This suggested that DMSO can be used in order to shorten the lag time of fingolimod permeation. However, the flux obtained from G declined after the 2 days. The balance between the amount of DMSO and other excipients, or between the solubility and the enhancement effect, will need to be further evaluated.

TABLE 2

| | % w/w | | | |
|---|---|---|---|---|
| Ingredients | D (3% FB/10% K90/DT9301) | E (3% FB/3% GMO/10% K90/DT9301) | F (3% FB/8% LL/10% K90/DT9301) | G (3% FB/8% LL/10% DMSO/7% ARS/DT9301) |
| Fingolimod base | 3 | 3 | 3 | 3 |
| Glyceryl monooleate | — | 3 | — | — |
| Lauryl lactate | — | — | 8 | 8 |
| Dimethylsulfoxide | — | — | — | 10 |
| Aerosil | — | — | — | 7 |
| PVP K90 | 10 | 10 | 10 | — |
| Duro-Tak 9301 adhesive | 87 | 84 | 79 | 72 |

3. Patch Example 3

Flux of Fingolimod Obtained from Fingolimod Base Formulations Prepared with PIB Adhesive The permeation of fingolimod obtained from fingolimod formulations in PIB adhesive was also evaluated. Due to the low solubility of fingolimod in the adhesive (less than 1%), PVP CLM was used as solubility aid and inhibitor of recrystallization. The other ingredients, i.e., Lauryl Lactate (LL), Glyceryl monooleate (GMO), Dimethyl sulfoxide (DMSO) were used as solubilizers and enhancers. In the formulation containing high percentage of liquid (formulation K), Aerosil (ARS) was added to increase the uniformity of the patch.

Figure 4:
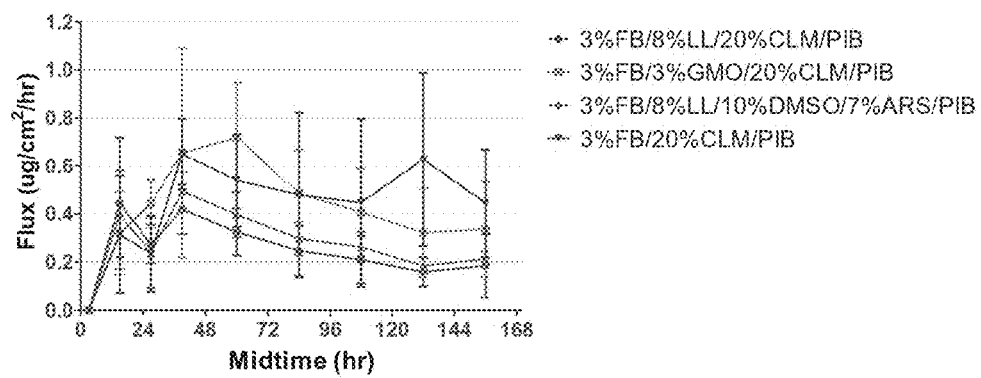

Using the general method described previously, fingolimod base formulations in PIB adhesive were prepared. The details of the ingredients in each formulation are shown in Table 3. The flux through human cadaver skin was measured and the results are presented in FIG. 4. The formulations in PIB adhesive also provide the permeation of fingolimod through the skin. The flux of formulations containing LL (J and K) appears to be lower than the flux of those formulations without LL (H and I). This observation could be due to the increase in solubility of drug when the LL is present in the formulations.

TABLE 3

| | % w/w | | | |
|---|---|---|---|---|
| Ingredients | H (3% FB/20% CLM/PIB) | I (3% FB/3% GMO/20% CLM/PIB) | J (3% FB/8% LL/20% CLM/PIB) | K (3% FB/8% LL/10% DMSO/7% ARS/20% CLM/PIB) |
| Fingolimod base | 3 | 3 | 3 | 3 |
| Glyceryl monooleate | — | 3 | — | — |
| Lauryl lactate | — | — | 8 | 8 |
| Dimethylsulfoxide | — | — | — | 10 |
| Aerosil | — | — | — | 7 |
| PVP CLM | 20 | 20 | 20 | — |
| PIB adhesive | 77 | 74 | 69 | 72 |

The flux results indicated that there is a lag time for the drug to first appear in the receptor solution following application of the formulation to the skin. This lag time could be caused by the binding properties of fingolimod onto the skin. The binding of fingolimod in the skin could result in deposition of fingolimod in the skin. As a result, fingolimod can be used locally and effectively in the treatment of dermatological disorders.

II. Topical Gel Formulations

A. Materials and Methods

1. Preparation of Formulations

1% Fingolimod hydrochloride gel formulations were prepared by dissolving the drug into water, then adding Hydroxypropyl methylcellulose (HPMC). The solutions were mixed thoroughly overnight until an homogeneous clear gel is formed. 0.25%, 0.5%, 0.75%, 1.0% and 2.0% Fingolimod hydrochloride gels were prepared by dissolving the required amount of drug into water.

2. Transdermal Flux Tests

Human cadaver skin was used and epidermal layers (stratum corneum and epidermis) were separated from the full-thickness skin as skin membrane and placed on top of the Franz cell. The donor compartment chamber and receptor sides of the Franz cell were clamped together. A receptor solution containing 0.9% sodium chloride was added to the cell. Solution samples or gel samples were inserted into the donor compartment chamber on top of the epidermis/stratum corneum. The cells were kept at a temperature of 33° C. during the entire experiment. Samples of the receptor solution were taken at regular intervals and the active agent concentration was measured by HPLC. The removed receptor solution was replaced with fresh solution to maintain the sink conditions. The flux was calculated from the slope of the cumulative amounts of the drug in the receiver compartment versus time.

3. Experimental Conditions

| | Example 1 | Example 2 | Example 3 |
|---|---|---|---|
| Membrane | Cadaver skin, Epidermis (IIAM, Rec'd Oct. 7, 2009 (Frozen Oct. 7, 2009), 5100900316-008; 33/W/F - Abdomen) | Cadaver skin, Epidermis (LGF, Rec'd Jan. 20, 2011 (Frozen Jan. 20, 2011), 10-10039; 92/W/F - Back) | Cadaver skin, Epidermis (LGF; Rec'd Jan. 20, 2011 (frozen January 2011, 10-11054; 83/W/F- Thigh) |
| Donor | 1% Fingolimod HCl gel | 0.5% Fingolimod HCl solution | 0.25, 0.5, 0.75, 1,2% Fingolimod HCl solution (Anode: Ag) |
| Receptor | 0.9% Sodium Chloride | 0.9% Sodium Chloride | 0.9% Sodium Chloride |
| Franz cell opening area | 1.77 cm2 | 1.77 cm2 | 1.77 cm2 |

|  | Example 1 | Example 2 | Example 3 |
|---|---|---|---|
| Duration | 3 days | 3 days | 2 days |
| Replicates | 3 | 3 | 3 |

B. Results

1. Gel Example 1

In-Vitro Permeation of Fingolimod Obtained from 1% Fingolimod Hydrochloride Gel

Figure 5A:
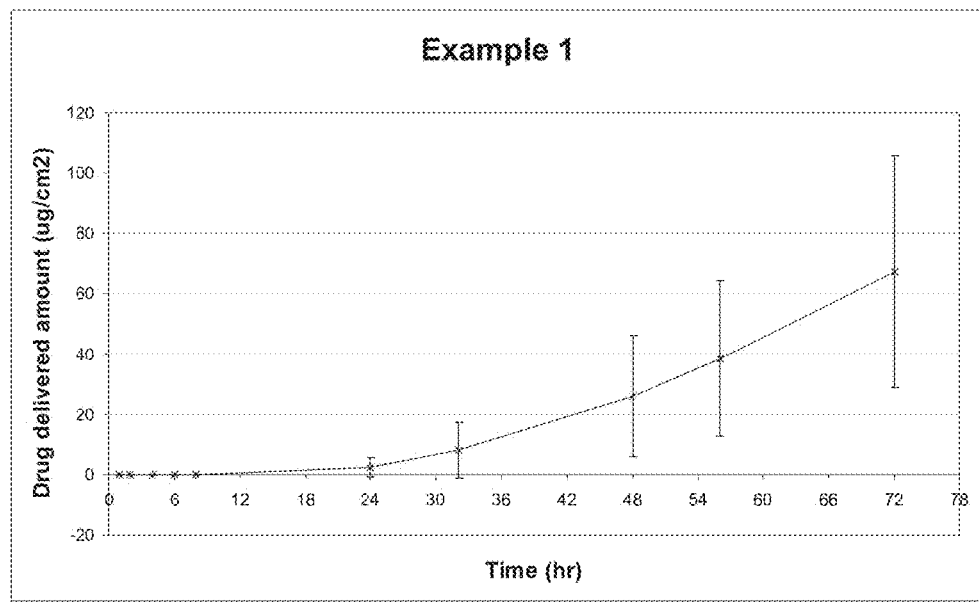
FIGS. 5A to 7B provide the results of transdermal flux tests performed on various topical gel formulations, as described in greater detail in the Experimental section, below.
Figure 5B:
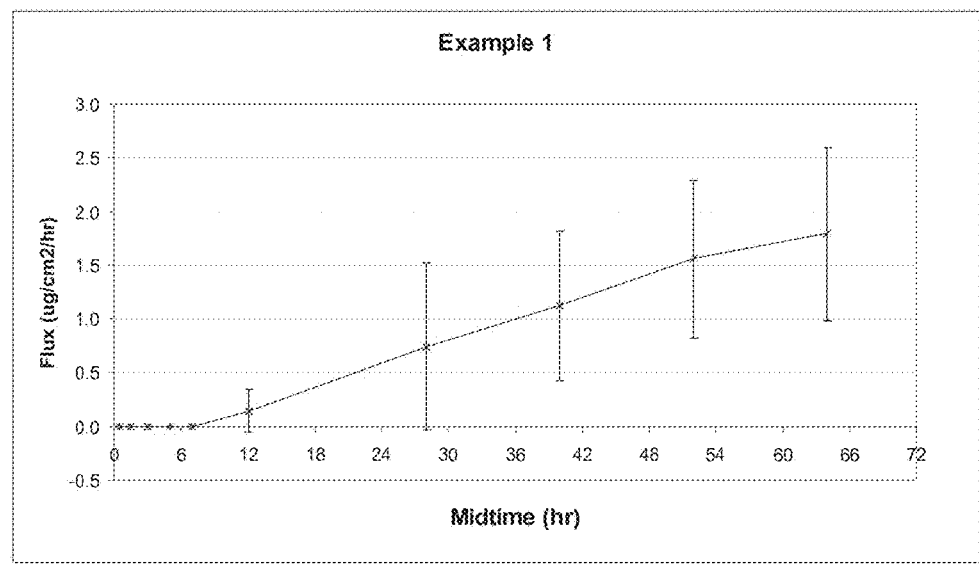

To evaluate fingolimod permeation through the skin, 1% fingolimod hydrochloride gel was made. HPMC was used to form the gel. The flux passing through the human cadaver skin was measured and the results are presented in FIGS. 5A and 5B.

2. Gel Example 2

Figure 6A:
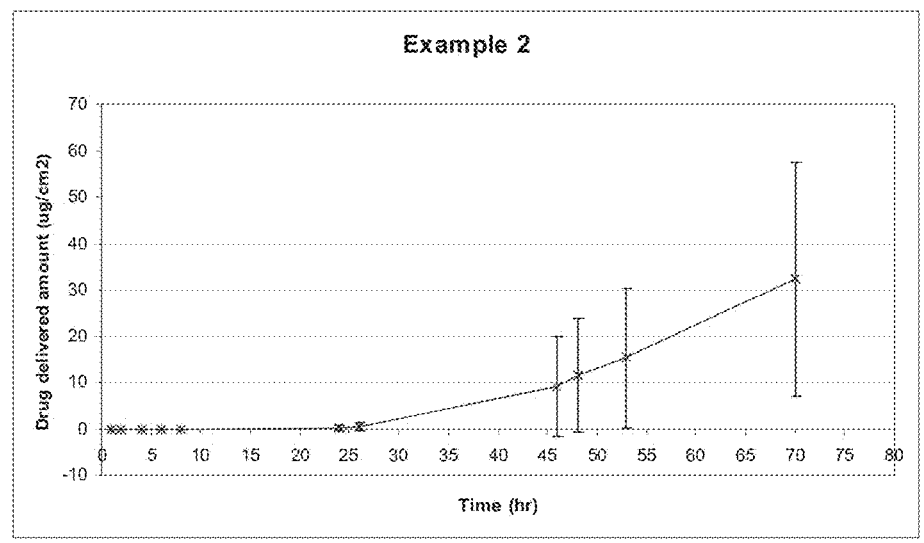
Figure 6B:
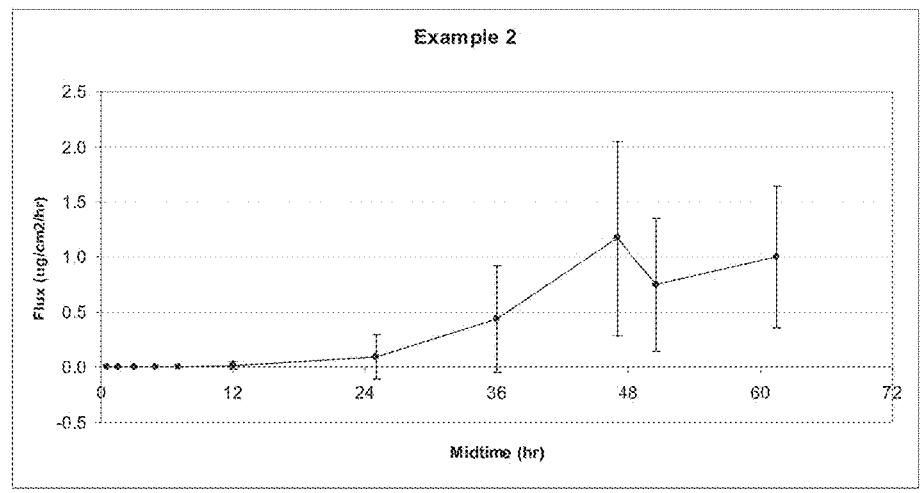

In-Vitro Permeation of Fingolimod Obtained from 0.5% Fingolimod Hydrochloride Solution The permeation of fingolimod from 0.5% fingolimod hydrochloride solution was also evaluated. The cumulative drug delivered amount and flux passing through the human cadaver skin was measured and the results are presented in FIGS. 6A and 6B.

3. Gel Example 3

Figure 7A:
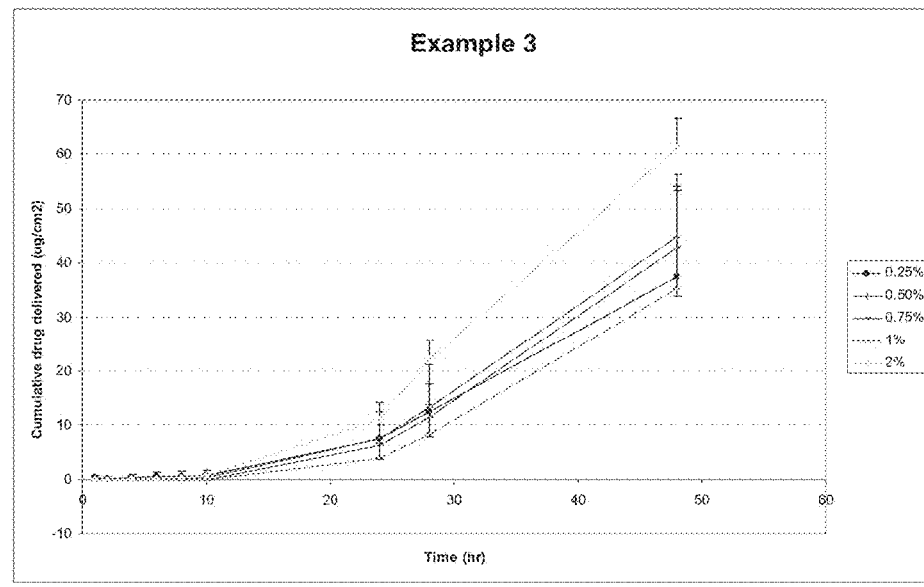
Figure 7B:
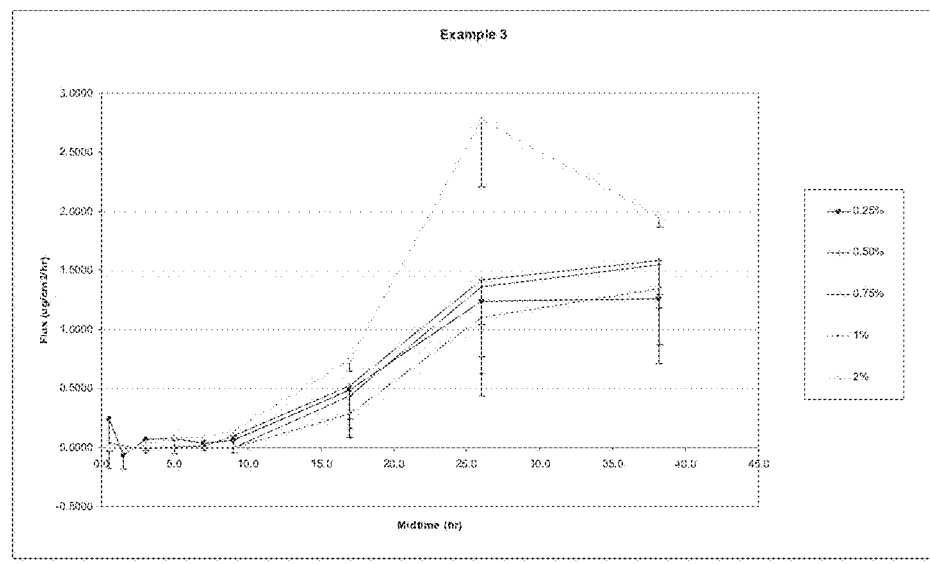

In-Vitro Permeation of Fingolimod Obtained from 0.25%, 0.5%, 0.75%, 1% and 2% Fingolimod Hydrochloride Solution The delivery of drug as a function of concentration was also evaluated. The flux through human cadaver skin was measured and the results are presented in FIGS. 7A and 7B. 0.25%, 0.5%, 0.75% and 1% fingolimod HCl showed similar cumulative drug delivered amount and fluxes of about 1-1.5 ug/cm2/hr during the 24-48 hours of the experiment. 2% fingolimod HCl appears to have a higher flux compared to the other lower concentration samples.

C. Discussion

During the first 8 hours of the experiments, Fingolimod was not detected in the receptor solutions. The flux results indicate that the drug took a long time to first appear in the receptor solution. Fingolimod appears to be significantly bound to either the stratum corneum or the viable epidermis. This retards the appearance of the drug in the receiving phase. The binding of fingolimod to the skin could generate substance deposition in the skin, and the resulting lag time of fingolimod by passive delivery through the skin is unusually long. As a result, fingolimod can be used locally and effectively in dermatological disorder.

The transportation of fingolimod hydrochloride through the skin could be through the shunt route. The presence of pores from the appendages (hair follicles, sweat ducts) might facilitate the contact between donor and receptor sites and contribute to the delivery of fingolimod HCl from the gel or solution into the receptor solution. In the present study, the deviation of the data seems high. This could be due to the difference in the presence of the pores in each skin piece and the micro-sized damage of the epidermis during the preparation of the epidermal membrane.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A topical patch comprising:
    an active agent layer comprising:
        a sphingosine-1-phosphate receptor agonist active agent;
        an acrylate pressure sensitive adhesive; and
        polyvinylpyrrolidone; and
    a backing layer.

2. The topical patch according to claim 1, wherein the topical patch is configured to provide extended delivery of the sphingosine-1-phosphate receptor agonist active agent.

3. The topical patch according to claim 1, wherein the sphingosine-1-phosphate receptor agonist active agent is 0.05% or more by weight of the active agent layer.

4. The topical patch according to claim 3, wherein the sphingosine-1-phosphate receptor agonist active agent is present in an amount ranging from 0.05 to 25% by weight of the active agent layer.

5. The topical patch according to claim 1, wherein the active agent layer comprises a permeation enhancer.

6. The topical patch according to claim 1, wherein the topical patch is configured so that the active agent layer contacts a skin area ranging in size from 2 cm$^2$ to 200 cm$^2$.

7. The topical patch according to claim 6, wherein the active agent layer has a thickness ranging from 20 μm to 200 μm.

8. The topical patch according to claim 1, wherein the topical patch is configured to deliver a systemic daily dosage of the sphingosine-1-phosphate receptor agonist.

9. The topical patch according to claim 1, wherein the topical patch is configured to deliver a local daily dosage of the sphingosine-1-phosphate receptor agonist.

10. The topical patch according to claim 9, wherein the local daily dosage of the sphingosine-1-phosphate receptor agonist active agent ranges from 0.0001 to 5.0 mg/day for 2 days or longer following application.

11. The topical patch according to claim 10, wherein the topical patch is configured to deliver a daily dosage of the sphingosine-1-phosphate receptor agonist active agent that ranges from 0.0001 to 5.0 mg/day for 3 to 7 days following application.

12. The topical patch according to claim 1, wherein the sphingosine-1-phosphate receptor agonist is a 2-amino-1,3-propanediol compound.

13. The topical patch according to claim 12, wherein the sphingosine-1-phosphate receptor agonist is fingolimod freebase or a salt thereof.

14. The topical patch according to claim 13, wherein the fingolimod salt is selected from the group consisting of: fingolimod HCl, fingolimod HBr, fingolimod maleate, fingolimod fumarate and combinations thereof.

15. A method of delivering a sphingosine-1-phosphate receptor agonist active agent to a subject, the method comprising:
(a) applying to skin of the subject a topical patch comprising:
an active agent layer comprising:
a sphingosine-1-phosphate receptor agonist active agent;
an acrylate pressure sensitive adhesive; and
polyvinylpyrrolidone; and
a backing layer
(b) maintaining the applied topical patch on the skin of the subject for a period of time sufficient to deliver the sphingosine-1-phosphate receptor agonist active agent to the subject.

16. A kit comprising two or more transdermal formulations according to claim 1.

17. The topical patch according to claim 1, wherein the active agent layer further comprises a homopolymer or copolymer comprising N-vinylpyrrolidone.

18. The topical patch according to claim 5, wherein the permeation enhancer is a compound selected from the group consisting of lauryl lactate, dodecyl pyrrolidone and glyceryl monooleate.

19. The topical patch according to claim 18, wherein the permeation enhancer is lauryl lactate.

20. The topical patch according to claim 18, wherein the permeation enhancer is dodecyl pyrrolidone.

21. The topical patch according to claim 18, wherein the permeation enhancer is glyceryl monooleate.

* * * * *